United States Patent
Morita et al.

(10) Patent No.: US 6,888,018 B2
(45) Date of Patent: May 3, 2005

(54) ORGANOMETALLIC COMPOUND HAVING HIGH METATHESIS ACTIVITY AND METHOD FOR PREPARATION THEREOF, METHATHESIS REACTION CATALYST COMPRISING THE COMPOUND, METHOD OF POLYMERIZATION USING THE CATALYST, AND POLYMER PRODUCED BY THE METHOD OF POLYMERIZATION

(75) Inventors: Takeharu Morita, Osaka (JP); Hiroshi Hiraike, Osaka (JP); Nobuhiro Goto, Kyoto (JP); Masafumi Nakatani, Kyoto (JP); Fumiyuki Ozawa, Osaka (JP); Hiroyuki Katayama, Osaka (JP)

(73) Assignee: Sekisui Chemical Co., Ltd., Osaka (JP)

( * ) Notice: Subject to any disclaimer, the term of this patent is extended or adjusted under 35 U.S.C. 154(b) by 0 days.

(21) Appl. No.: 10/363,045

(22) PCT Filed: Aug. 20, 2001

(86) PCT No.: PCT/JP01/07401

§ 371 (c)(1),
(2), (4) Date: Jun. 19, 2003

(87) PCT Pub. No.: WO02/18399

PCT Pub. Date: Mar. 7, 2002

(65) Prior Publication Data

US 2004/0015002 A1 Jan. 22, 2004

(30) Foreign Application Priority Data

| Aug. 31, 2000 | (JP) | 2000-262822 |
| Jun. 26, 2001 | (JP) | 2001-193103 |
| Aug. 24, 2001 | (JP) | 2001-25434 |

(51) Int. Cl.$^7$ .......................... C07F 15/00; B01J 31/00
(52) U.S. Cl. .......................... 556/11; 556/12; 556/136; 548/101; 526/90; 526/92; 526/93; 526/126; 502/152; 502/162; 502/167
(58) Field of Search .......................... 556/11, 12, 136; 548/101; 526/90, 92, 93, 126; 502/152, 162, 167

(56) References Cited

FOREIGN PATENT DOCUMENTS

| JP | 2001-302888 | 10/2001 |
| WO | WO 97/6185 A1 | 2/1997 |
| WO | WO 98/393346 A1 | 9/1998 |

OTHER PUBLICATIONS

H. Katayama et al.; Chemistry Letters, 1998 (1), 67–68. Cited in the Int'l. search rpt.
K. Karlou–Eyrisch et al.; Journal of Organometallic Chemistry, 606(1) 3–7, (2000). Cited in the Int'l. search rpt.
D. Huang et al.; Organometallics, 19(10), 1967–72 (2000). Cited in the Int'l. search rpt.
P. Barbaro et al.; Inorganica Chimica Acta, 220 (1–2), 5–19 (1994). Cited in the Int'l. search rpt.
V. Heroguez, et al.; Macromol. Chem. Phys., 199(7), 1405–12 (1998). Cited in the Int'l. search rpt.
H. Katayama et al.; Organometallics, 17(23), 5190–6 (1998). Cited in the Int'l. search rpt.
D. Huang et al.; Organometallics, 17(21), 4700–6 (1998). Cited in the Int'l. search rpt.
M. Olivan et al.; Organometallics, 16(11), 2227–9 (1997). Cited in the Int'l. search rpt.
M. Olivan et al.; Organometallics, 17(14), 3091–3100 (1998). Cited in the Int'l. search rpt.

*Primary Examiner*—Porfirio Nazario-Gonzalez
(74) *Attorney, Agent, or Firm*—Armstrong, Kratz, Quintos, Hanson & Brooks, LLP

(57) ABSTRACT

The present invention provides an organometallic compound represented by the general formula (1) or (2), process for producing the same, metathesis reaction catalyst containing the same, polymerization process using the same catalyst and polymer produced by the same polymerization process:

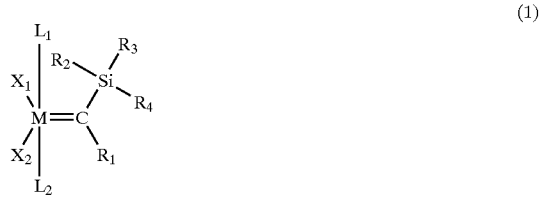

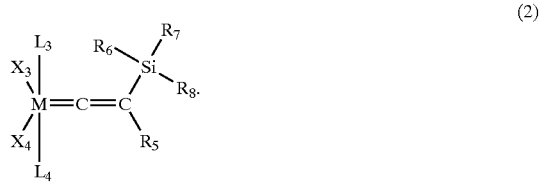

20 Claims, No Drawings

ORGANOMETALLIC COMPOUND HAVING HIGH METATHESIS ACTIVITY AND METHOD FOR PREPARATION THEREOF, METHATHESIS REACTION CATALYST COMPRISING THE COMPOUND, METHOD OF POLYMERIZATION USING THE CATALYST, AND POLYMER PRODUCED BY THE METHOD OF POLYMERIZATION

TECHNICAL FIELD

The present invention relates to a novel organometallic compound of high metathesis activity, process for producing the same, metathesis reaction catalyst containing the same, polymerization process using the same catalyst and polymer produced by the same polymerization process, more particularly a novel organometallic compound excellent in stability to oxygen, metathesis reactivity and reaction controllability, process for producing the same, metathesis reaction catalyst containing the same, polymerization process using the same catalyst and polymer produced by the same polymerization process.

BACKGROUND ART

The metathesis reaction has been widely used in various industrial areas, e.g., for synthesis of monomers for the medical area, and production of molded articles excellent in mechanical strength, heat resistance, dimensional stability or the like by ring-opening polymerization in a mold, e.g., by reaction injection molding (hereinafter sometimes referred to as RIM), of a norbornene-based monomer, e.g., dicyclopentadiene (hereinafter sometimes referred to as DCPD), which is a typical representative monomer for metathesis polymerization.

The conventional metathesis process uses a catalyst which exhibits the metathesis activity by reacting the catalyst precursor for the active catalyst, e.g., molybdenum or tungsten, with an alkyl metal in a system, as disclosed by, e.g., Japanese Patent No.3,038,825. However, such a process is greatly limited by, e.g., reaction environments, because the alkyl metal is a water-reactive reagent.

Japanese Patent Laid-Open No.11-510807 discloses a ruthenium-based metathesis catalyst as the one which can solve the above problems. It has been attracting attention as a catalyst exhibiting excellent metathesis activity without being deactivated even in the presence of moisture or oxygen. However, it is not activated as an alkyl metal or the like in a system but exhibits activity as a single complex compound. As a result, the reaction starts as soon as it is brought into contact with a metathesis-reactive monomer, to cause problems, one of which is dispersion of the catalyst or the like becoming the rate-determining step. This may be a detrimental problem when a crosslinkable monomer, e.g., dicyclopentadiene, is to be polymerized, because this can greatly limit the process operation or fluctuate properties of the product polymer. One of the commonly known countermeasures is incorporation of triphenyl phosphine or the like in the system to retard the polymerization process. This, however, may cause problems related to product safety, resulting from contamination of the product with phosphorus or the like.

It is an object of the present invention to provide a novel organometallic compound excellent in stability to oxygen, methathesis reactivity and reaction controllability, in order to solve the above problems. It is another object of the present invention to provide a process for producing the same. It is still another object of the present invention to provide a metathesis reaction catalyst containing the same. It is still another object of the present invention to provide a polymerization process using the same catalyst. It is still another object of the present invention to provide a polymer produced by the same polymerization process.

DISCLOSURE OF THE INVENTION

The inventors have prepared, after having extensively studied to solve the problems involved in the conventional metathesis reaction catalyst, a novel organometallic compound containing ruthenium or osmium and silicon to find that it is excellent in stability to oxygen, reaction controllability and metathesis reactivity. The present invention is developed based on this knowledge.

The first aspect of the present invention provides an organometallic compound containing ruthenium or osmium and silicon, represented by the general formula (1):

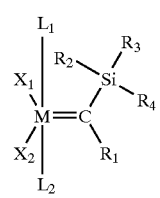

(1)

wherein, M is ruthenium or osmium; $R_1$ is hydrogen atom, an alkenyl group of 2 to 20 carbon atoms, alkyl group of 1 to 20 carbon atoms, aryl group of 6 to 20 carbon atoms, carboxyl group of 2 to 20 carbon atoms, alkoxy group of 2 to 20 carbon atoms, alkenyloxy group of 2 to 20 carbon atoms, aryloxy group of 6 to 20 carbon atoms, alkoxycarbonyl group of 2 to 20 carbon atoms, alkyithia group of 2 to 20 carbon atoms, alkylsilyl group of 2 to 20 carbon atoms, arylsilyl group of 2 to 20 carbon atoms or ferrocene derivative, as required, with a phenyl group substituted with an alkyl group of 1 to 5 carbon atoms, halogen atom or alkoxy group of 1 to 5 carbon atoms; $R_2$ to $R_4$ are each hydrogen atom, an alkenyl group of 2 to 20 carbon atoms, alkyl group of 2 to 20 carbon atoms, aryl group of 6 to 20 carbon atoms, carboxyl group of 2 to 20 carbon atoms, alkoxy group of 2 to 20 carbon atoms, alkenyloxy group of 2 to 20 carbon atoms, aryloxy group of 6 to 20 carbon atoms, alkoxycarbonyl group of 2 to 20 carbon atoms, alkylthio group of 2 to 20 carbon atoms, alkylsilyl group of 2 to 20 carbon atoms, arylsilyl group of 2 to 20 carb atoms or ferrocene derivative, which may be the same or different and substituted, as required with a phenyl group substituted with an alkyl group of 1 to 5 carbon atoms, halogen atom or alkoxy group of 1 to 5 carbon atoms; when $R_1$ is hydrogen atom, at least one of $R_2$ to $R_4$ is phenyl, isopropyl or t-butyl group; $X_1$ and $X_2$ are each an anionic ligand, which maybe the same or different; and $L_1$ and $L_2$ are each a neutral electron donor, which may be the same or different and at least one of $L_1$ and $L_2$ is a phosphorus-based ligand; where 2 or 3 of $X_1$, $X_2$, $L_1$ and $L_2$ may together form a multidentate, chelated ligand.

The second aspect provides the organometallic compound of the first aspect, wherein $R_1$ in the general formula (1) is a substituent selected from the group consisting of phenyl, anisyl, t-butyl, n-butyl, n-propyl, isopropyl, ethyl, methyl, methoxyrnethyl, ferrocenyl and trimethylsilyl group; the third aspect provides the organometallic compound of the first aspect, wherein each of $R_2$ to $R_4$ in the general formula (1) is a substituent selected from the group consisting of methyl, ethyl, isopropyl, t-butyl, cyclohexyl and phenyl group; and the fourth aspect provides the organometallic compound of the first aspect, wherein each of $L_1$ and $L_2$ in the general formula (1) is a phosphorus-based ligand.

The fifth aspect of the present invention provides an organometallic compound containing ruthenium or osmium and silicon, represented by the general formula (2):

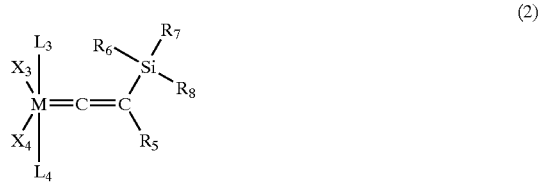

wherein, M is ruthenium or osmium; $R_5$ is hydrogen atom, an alkenyl group of 2 to 20 carbon atoms, alkyl group of 1 to 20 carbon atoms, substituted phenyl group of 7 to 20 carbon atoms, carboxyl group of 2 to 20 carbon atoms, alkoxy group of 2 to 20 carbon atoms, alkenyloxy group of 2 to 20 carbon atoms, aryloxy group of 6 to 20 carbon atoms, alkoxycarbonyl group of 2 to 20 carbon atoms, alkylthio group of 2 to 20 carbon atoms, alkylsilyl group of 2 to 20 carbon atoms or arylsilyl group of 2 to 20 carbon atoms; $R_6$ to $R_8$ are each hydrogen atom, an alkenyl group of 2 to 20 carbon atoms, alkyl group of 1 to 20 carbon atoms, aryl group of 6 to 20 carbon atoms, carboxyl group of 2 to 20 carbon atoms, alkoxy group of 2 to 20 carbon atoms, alkenyloxy group of 2 to 20 carbon atoms, aryloxy group of 6 to 20 carbon atoms, alkoxycarbonyl group of 2 to 20 carbon atoms, alkylthio group of 2 to 20 carbon atoms, alkylsilyl group of 2 to 20 carbon atoms, arylsilyl group of 2 to 20 carbon atoms or ferrocene derivative, which may be the same or different and substituted, as required, with a phenyl group substituted with an alkyl group of 1 to 5 carbon atoms, halogen atom or alkoxy group of 1 to 5 carbon atoms; when $R_5$ is hydrogen atom, at least one of $R_6$ to $R_8$ is phenyl, isopropyl or t-butyl group; $X_3$ and $X_4$ are each a halogen atom, which may be the same or different; and $L_3$ and $L_4$ are each a neutral electron donor, which may be the same or different; where 2 or 3 of $X_3$, $X_4$, $L_3$ and $L_4$ may together form a multidentate, chelated ligand.

The sixth aspect provides the organometallic compound of the fifth aspect, wherein $R_5$ in the general formula (2) is a substituent selected from the group consisting of tolyl, anisyl, t-butyl, n-butyl, n-propyl, isopropyl, ethyl, methyl, methoxymethyl and trimethylsilyl group; the seventh aspect provides the organometallic compound of the fifth aspect, wherein each of $R_6$ to $R_8$ in the general formula (2) is a substituent selected from the group consisting of methyl, ethyl, isopropyl, t-butyl, cyclohexyl and phenyl group; and the eighth aspect provides the organometallic compound of the fifth aspect, wherein each of $L_3$ and $L_4$ in the general formula (2) is a phosphorus-based ligand.

The ninth aspect of the present invention provides a process for producing the organometallic compound of one of the first to eighth aspects, wherein a precursor for a ruthenium or osmium complex and neutral electron-donating ligand compound are mixed with each other for the ligand-exchanging reaction.

The tenth aspect of the present invention provides a metathesis reaction catalyst containing the organometallic compound of one of the first to eighth aspects.

The 11$^{th}$ aspect of the present invention provides a metathesis polymerization process for producing a metathesis-reactive monomer in the presence of the metathesis reaction catalyst of the tenth aspect.

The 12$^{th}$ aspect of the present invention provides the metathesis polymerization process of the 11$^{th}$ aspect, wherein the metathesis-reactive monomer is a norbornene-based monomer of bicyclic or higher structure; the 13$^{th}$ aspect of the present invention provides the metathesis polymerization process of the 11$^{th}$ aspect, wherein the norbornene-based monomer is a compound selected from the group consisting of norbornene, substituted norbornene, dicyclopentadiene and tricyclopentadiene; the 14$^{th}$ aspect of the present invention provides the metathesis polymerization process of one of the 11$^{th}$ to 13$^{th}$ aspects, wherein 2 or more metathesis-reactive monomers are copolymerized.

The 15$^{th}$ aspect of the present invention provides the metathesis polymerization process of one of the 11$^{th}$ to 14$^{th}$ aspects, wherein a reaction-adjusting agent is further incorporated.

The 16$^{th}$ aspect of the present invention provides the metathesis polymerization process of the 15$^{th}$ aspect, wherein the reaction-adjusting agent is an acidic component; and the 17$^{th}$ aspect of the present invention provides the metathesis polymerization process of 16$^{th}$ aspect, wherein the acidic component is a Bronsted acid (protonic acid).

The 18$^{th}$ aspect of the present invention provides the metathesis polymerization process of one of the 11$^{th}$ to 17$^{th}$ aspects, wherein a reaction-controlling agent is further incorporated.

The 19$^{th}$ aspect of the present invention provides the metathesis polymerization process of the 18$^{th}$ aspect, wherein the reaction-controlling agent is a compound having a metathesis-reactive unsaturated bond; the 20$^{th}$ aspect of the present invention provides the metathesis polymerization process of 19$^{th}$ aspect, wherein the compound having a metathesis-reactive unsaturated bond is selected from the group consisting of a vinyl ester, vinyl sulfide, vinyl ether, vinyl pyrrolidone, allyl ester and allyl sulfide.

The 21$^{st}$ aspect of the present invention provides the polymer produced by the polymerization process of one of the 11$^{th}$ to 20$^{th}$ aspects.

The 22$^{nd}$ aspect of the present invention provides the polymer of the 21$^{st}$ aspect, whose molecular weight is controlled by a reaction-controlling agent; the 23$^{rd}$ aspect of the present invention provides the polymer of the 21$^{st}$ aspect, wherein an anti-oxidant is incorporated in the polymerization system.

BEST MODE FOR CARRYING OUT THE INVENTION

The present invention is described in detail below.
1. Organometallic Compound

The first aspect of the present invention is an organometallic compound (hereinafter referred to as First Organometallic Compound) containing ruthenium or osmium and silicon, represented by the general formula (1):

Wherein, M is ruthenium or osmium; $R_1$ to $R_4$ are each hydrogen atom, an alkenyl group of 2 to 20 carbon atoms, alkyl group of 1 to 20 carbon atoms, aryl group of 6 to 20 carbon atoms, carboxyl group of 2 to 20 carbon atoms, alkoxy group of 2 to 20 carbon atoms, alkenyloxy group of 2 to 20 carbon atoms, aryloxy group of 6 to 20 carbon atoms, alkoxycarbonyl group of 2 to 20 carbon atoms, alkylthio group of 2 to 20 carbon atoms, alkylsilyl group of 2 to 20 carbon atoms, arylsilyl group of 2 to 20 carbon atoms or ferrocene derivative, which may be the same or different and substituted, as required, with a phenyl group substituted with an alkyl group of 1 to 5 carbon atoms, halogen atom or alkoxy group of 1 to 5 carbon atoms; $X_1$ and $X_2$ are each an anionic ligand, which may be the same or different; and $L_1$ and $L_2$ are each a neutral electron donor, which may be the same or different; where 2 or 3 of $X_1$, $X_2$, $L_1$ and $L_2$ may together form a multidentate, chelated ligand.

The substituent $R_1$ is preferably the one other than hydrogen atom in the above range, viewed from stability and catalytic activity of the organometallic compound. In other words, catalytic activity of an organometallic compound, when used for a metathesis reaction, is greatly affected by electron density of the central metal, increasing electron density improving its affinity for the reaction matrix and hence reaction activity. Therefore, the substituent is preferably other than hydrogen atom, viewed from catalytic activity. An organometallic compound has greatly improved stability as its bulk density increases. Therefore, the substituent is preferably other than hydrogen atom, also viewed from stability.

More specifically, the substituents represented by $R_1$ preferable for improving electron density of the metal include phenyl, t-butyl, n-butyl, n-propyl, isopropyl, ethyl and methyl group. A phenyl group substituted with an electron-donating group (e.g., alkyl or alkoxy group) is more preferable, because it can improve electron density of the metal more efficiently. These groups include tolyl and anisyl group.

The other preferable substituents represented by $R_1$ include methoxymethyl, ferrocenyl and trimethylsilyl (TMS) group, because they push electrons onto the metal.

Each of the substituents $R_2$ to $R_4$ is preferably selected from the group consisting of methyl, ethyl, isopropyl, t-butyl, cyclohexyl and phenyl group, because they can be bonded to a silicon atom while overlapping each other.

When $R_1$ is hydrogen atom, in particular, the organometallic compound preferably contains phenyl, isopropyl, t-butyl group or the like, because of its effect of stabilizing the compound. When $R_1$ is other than hydrogen atom, on the other hand, even methyl group as each of the substituents $R_2$ to $R_4$ can allow the metathesis reaction to proceed, because the organometallic compound can be stably present.

$L_1$ and $L_2$ are each a neutral electron donor, as described earlier, and preferably a phosphorus -based ligand. The preferable phosphorus-based ligands include a phosphine represented by the formula $PR_9R_{10}R_{11}$, wherein $R_9$, $R_{10}$ and $R_{11}$ are each an alkyl group of 1 to 20 carbon atoms or aryl group of 6 to 20 carbon atoms, preferably methyl, ethyl, isopropyl, t-butyl, cyclohexyl, phenyl or substituted phenyl. $R_9$, $R_{10}$ and $R_{11}$ may be the same or different.

More specifically, $L_1$ and $L_2$ may be each —P(cyclohexyl)$_3$, —P(phenyl)$_3$ or —P(isopropyl)$_3$.

$X_1$ and $X_2$ in the general formula (1) may be selected from any anionic ligands, preferably Cl or Br, the former being more preferable.

First Organometallic Compound of the present invention can be produced by various processes. One of the processes produces the objective organometallic compound represented by the formula (1) by the ligand-exchanging reaction according to the reaction (i) between a ruthenium or osmium complex precursor as one of the starting compounds and neutral electron-donating ligand compound as the other starting compound, each starting compound being produced by a known process.

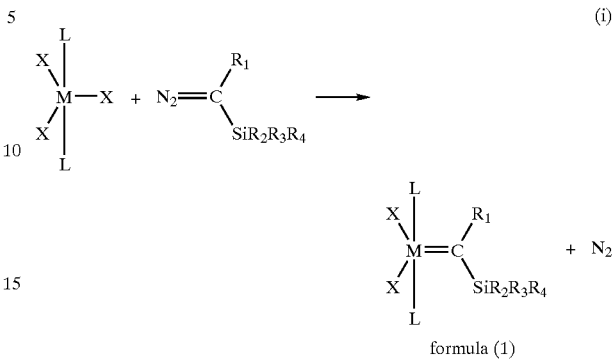

formula (1)

The reaction (i) is effected at a low temperature (e.g., −78° C.) in an organic solvent (e.g., dichloromethane), because a diazomethane derivative as one of the starting compounds is a very unstable compound with nitrogen easily eliminated to form a carbene species, which reacts with the metal.

The fifth aspect of the present invention, on the other hand, is an organometallic compound (hereinafter referred to as Second Organometallic Compound) containing ruthenium or osmium and silicon, represented by the general formula (2):

$$\begin{array}{c} L_3 \quad R_6 \diagdown \diagup R_7 \\ X_3 \diagdown \quad \quad Si \\ \diagdown \quad \diagup \quad \diagdown R_8 \\ M = C = C \\ \diagup \quad \diagdown \\ X_4 \quad \quad R_5 \\ L_4 \end{array} \qquad (2)$$

Wherein, M is ruthenium or osmium; $R_5$ to $R_8$ are each hydrogen atom, an alkenyl group of 2 to 20 carbon atoms, alkyl group of 1 to 20 carbon atoms, aryl group of 6 to 20 carbon atoms, carboxyl group of 2 to 20 carbon atoms, alkoxy group of 2 to 20 carbon atoms, alkenyloxy group of 2 to 20 carbon atoms, aryloxy group of 6 to 20 carbon atoms, alkoxycarbonyl group of 2 to 20 carbon atoms, alkylthio group of 2 to 20 carbon atoms, alkylsilyl group of 2 to 20 carbon atoms, arylsilyl group of 2 to 20 carbon atoms or ferrocene derivative, which may be the same or different and substituted, as required, with a phenyl group substituted with an alkyl group of 1 to 5 carbon atoms, halogen atom or alkoxy group of 1 to 5 carbon atoms; $X_3$ and $X_4$ are each an anionic ligand, which may be the same or different; and $L_3$ and $L_4$ are each a neutral electron donor, which may be the same or different; where 2 or 3 of $X_3$, $X_4$, $L_3$ and $L_4$ may together form a multidentate, chelated ligand.

The substituent $R_5$ is preferably the one other than hydrogen atom in the above range, viewed from stability and catalytic activity of the organometallic compound. In other words, catalytic activity of an organometallic compound, when used for a metathesis reaction, is greatly affected by electron density of the central metal, increasing electron density improving its affinity for the reaction matrix and hence reaction activity. Therefore, the substituent $R_5$ is preferably other than hydrogen atom, viewed from catalytic activity. An organometallic compound has greatly improved stability as its bulk density increases. Therefore, the substituent is preferably other than hydrogen atom, also viewed from stability.

More specifically, the substituents represented by $R_5$ preferable for improving electron density of the metal include phenyl, t-butyl, n-butyl, n-propyl, isopropyl, ethyl and methyl group. A phenyl group substituted with an electron-donating group (e.g., alkyl or alkoxy group) is more preferable, because it can improve electron density of the metal more efficiently. These groups include tolyl and anisyl group.

The other preferable substituents represented by $R_5$ include methoxymethyl, ferrocenyl and trimethylsilyl (TMS) group, because they push electrons onto the metal.

Each of the substituents $R_6$ to $R_8$ is preferably selected from the group consisting of methyl, ethyl, isopropyl, t-butyl, cyclohexyl and phenyl group, because they can be bonded to a silicon atom while overlapping each other.

When $R_5$ is hydrogen atom, in particular, the organometallic compound preferably contains phenyl, isopropyl, t-butyl group or the like, because of its effect of stabilizing the compound. When $R_5$ is other than hydrogen atom, on the other hand, even methyl group as each of the substituents $R_6$ to $R_8$ can allow the metathesis reaction to proceed, because the organometallic compound can be stably present.

$L_3$ and $L_4$ are each a neutral electron donor, as described earlier, and preferably a phosphorus-based ligand. The preferable phosphorus-based ligands include a phosphine represented by the formula $PR_{12}R_{13}R_{14}$, wherein $R_{12}$, $R_{13}$ and $R_{14}$ are each an alkyl group of 1 to 20 carbon atoms or aryl group of 6 to 20 carbon atoms, preferably methyl, ethyl, isopropyl, t-butyl, cyclohexyl, phenyl or substituted phenyl. They may be the same or different.

More specifically, $L_3$ and $L_4$ may be each —P(cyclohexyl)$_3$, —P(phenyl)$_3$ or —P(isopropyl)$_3$, among others.

$X_3$ and $X_4$ in the general formula (2) may be optionally selected from anionic ligands, preferably Cl or Br, the former being more preferable.

Chem. Lett., 1998, page 67, illustrates some organometallic compounds corresponding to the general formula (2) and describes the metathesis polymerization which uses these compounds. However, this article merely scientifically predicts the compounds, considered to be intermediately formed in the reaction system, and does not isolate or confirm the complexes. These compounds are apparently different from the organometallic compound of the present invention, which is isolated to confirm its structure chemically and physicochemically, and its metathesis catalyst function.

Second Organometallic Compound of the present invention can be produced by various processes. One of the processes produces the objective organometallic compound represented by the formula (2) by the ligand-exchanging reaction and rearrangement according to the reaction (ii) or (iii) between a ruthenium or osmium complex precursor as one of the starting compounds and neutral electron-donating ligand compound as the other starting compound, each starting compound being produced by a known process.

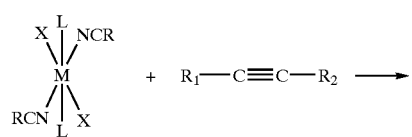

(ii)

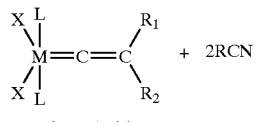

formula (2)

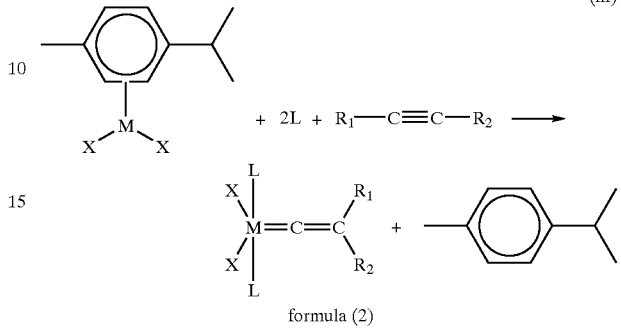

formula (2)

Each of the reactions (ii) and (iii) proceeds easily under conditions of, e.g., at normal temperature to 80° C. in an organic solvent, e.g., dichloromethane, dichloroethane, toluene or THF.

2. Metathesis Reaction Catalyst

Each of First and Second Organometallic Compounds of the present invention (hereinafter sometimes referred to generically as the organometallic compound of the present invention) can be suitably used for the metathesis reaction.

The metathesis reactions include a structural change within the same monomer having an unsaturated bond, cross-metathesis reaction between monomers having an unsaturated bond, and metathesis polymerization. The metathesis polymerization may be ring-opening or non-cyclic type.

Second Organometallic Compound of the present invention is more suitably used than First Organometallic Compound, because of its better reaction controllability.

The organometallic compound of the present invention, when used for the metathesis reaction, may be incorporated with a reaction-adjusting agent in the reaction process. Use of such an agent can control reaction rate. The agent can accelerate or decelerate the metathesis reaction, when its type and content are adequately set. The reaction-adjusting agent is not limited. However, an acidic component is particularly preferable, when the reaction is to be accelerated.

The acid component useful for the present invention as the reaction-adjusting agent is not limited. A so-called Brosnted acid (protonic acid) can be used. Examples of these acids include hydrochloric, sulfuric, nitric, acetic and formic acid, and ammonium chloride in the form of aqueous solution. The acid component may decompose the organometallic compound itself, depending on type of the organometallic compound or metathesis-reactive monomer used, to deactivate the catalyst. It is therefore preferable to incorporate a weak acid of very low acidity selected from the above acid components. A chlorine-based solvent may be also used as a solvent of very low acidity. Methylene chloride, for example, may be used as the chlorine-based solvent. Moreover, the reaction system can be kept weakly acidic in the presence of silica gel, which is used for column chromatography.

Content of the reaction-adjusting agent is not limited. However, it is incorporated normally at 10 to $^1/_{10,000}$ equivalents per equivalent of the organometallic compound of the present invention working as the metathesis reaction catalyst, preferably 1 to $^1/_{100}$ equivalents.

The organometallic compound of the present invention, when used for the metathesis reaction, may be incorporated with a reaction-controlling agent in the reaction process. Use of such an agent can control molecular weight of the product polymer. It can freely control the molecular weight, when its type and content (its ratio to the monomer) are adequately set. The reaction-controlling agent is preferably a compound having a metathesis-reactive unsaturated bond, in particular a compound containing a hetero element.

The compound having a metathesis-reactive unsaturated bond, useful for the present as the reaction-controlling agent, is not limited. Examples of these compounds include vinyl ester, vinyl sulfide, vinyl ether, vinyl pyrrolidone, allyl ester and allyl sulfide.

Content of the reaction-controlling agent is not limited, and varies depending on molecular weight of the objective polymer. However, it is incorporated normally at $1/2$ to $1/10,000$ equivalents per equivalent of the metathesis-reactive monomer, preferably $1/2$ to $1/1000$ equivalents.

The organometallic compound of the present invention is more stable in air, stable to a functional or polar group, and resistant to heat than the conventional metathesis reaction catalyst. When used for metathesis polymerization, it can greatly reduce quantity of the monomer remaining after the polymerization process with the above favorable characteristics.

The metathesis process proceeding in the presence of the organometallic compound of the present invention may be effected in a solvent. An organic solvent which can dissolve the metathesis-reactive monomer is preferable, when the reaction is effected in a homogeneous system. Examples of these solvents include toluene, benzene, chloroform, hexane and xylene. The reaction may be effected in a heterogeneous system. A solvent which little dissolves the metathesis-reactive monomer, e.g., water, can be also used, because the organometallic compound of the present invention is stable to hydrogen or oxygen. Moreover, suspension or dispersion polymerization can be adopted in the presence of a dispersion stabilizer or the like.

The reaction conditions of the metathesis reaction effected in the presence of the organometallic compound of the present invention are described. Content of the organometallic compound of the present invention is preferably $1/5$ to $1/500,000$ equivalents per equivalent of the whole metathesis-reactive monomer(s). At above $1/5$ equivalents, the polymer product may not have a sufficient molecular weight, when it is used for a polymerization process. At below $1/500,000$ equivalents, on the other hand, the reaction may not proceed at a sufficient rate, and hence is undesirable. More preferably $1/30$ to $1/200,000$ equivalents per equivalent of the whole metathesis-reactive monomer(s).

Reaction temperature of the metathesis reaction effected in the presence of the organometallic compound of the present invention varies depending on melting point and boiling point of the compounds used for the process, e.g., metathesis-reactive monomer, solvent, reaction-adjusting agent and reaction-controlling agent. However, it is preferably −30 to 170° C., more preferably −30 to 150° C.

3. Metathesis Polymerization Process and Polymer

The organometallic compound of the present invention is suitable as a catalyst for metathesis polymerization, ring-opening or non-cyclic, as described earlier. When the organometallic compound of the present invention is used for ring-opening metathesis polymerization, the monomer for the polymerization is not limited. The useful cyclic, unsaturated compounds include polycyclic, unsaturated compounds, e.g., norbornene and its derivatives and dicyclopentadiene and its derivatives, and cyclobutene, cyclohexene, cyclooctene and cyclooctadiene.

For norbornene and its derivatives, the preferable ones for the present invention are polycyclic norbornene-based monomers of bicyclic or higher structure. Such a monomer gives a norbornene-based polymer of high thermal deformation temperature.

The bicyclic norbornene-based monomer is not limited. Some of the examples include 2-norbornene, 5-methyl-2-norbornene, 5-ethylidene-2-norbornene and 5-phenyl norbornene.

The polycyclic norbornene-based monomer of tricyclic or higher structure is also not limited. Some of the examples are tricyclic ones, e.g., dicyclopentadiene (DCPD) and dihydroxypentadiene; tetracyclic ones, e.g., tetracyclododecene; pentacyclic ones, e.g., tricyclopentadiene; heptacyclic ones, e.g., tetracyclopentadiene; alkyl-substituted polycyclic monomers, e.g., methyl-, ethyl-, propyl- and butyl-substituted ones; alkylidene-substututed ones, e.g., ethylidene-substituted ones; and aryl-substituted ones, e.g., phenyl-, tolyl- and naphthyl-substituted ones. These norbornene-based monomers may be used either individually or in combination. Of these, more preferable ones are crosslinkable monomers of dicyclopentadiene and tricyclopentadiene, viewed from their availability, reactivity, heat resistance and so on, because they are excellent in reaction rate controllability and high reactivity.

Moreover, the organometallic compound of the present invention can be used for metathesis polymerization of a monomer containing a functional group. The functional groups for these monomers are widely varying, and may be polar or non-polar. They include hydroxyl, carboxyl, amino, ester, acetoxy, alkoxy, halogen, carbonyl, mercapto, epoxy, silyl, oxazoline, sulfonate, maleimide, azlactone and vinyl, to begin with.

When the organometallic compound of the present invention is used for metathesis polymerization, polymerization of a norbornene-based monomer is one example in which high heat resistance as one of the characteristics of the organometallic compound is fully utilized. The conventional polymerization catalyst, when used for polymerization of a norbornene-based monomer, will be partly deactivated due to a large quantity of heat released by the exothermic reaction, unless it is in the form of diluted solution. On the other hand, the organometallic compound of the present invention loses the catalytic activity to a lesser extent, and leaves the unreacted monomer also to a lesser extent after completion of the polymerization process. These favorable effects will be more noted when it is used for polymerization of dicyclopentadiene as the monomer.

Polymerization of a norbornene-based monomer as a metathesis-reactive monomer is effected preferably at −20 to 220° C. At below −20° C., a norbornene-based monomer may be too low in fluidity to smoothly incorporate the organometallic compound of the present invention. On the other hand, polymerization temperature of above 220° C. is undesirable, because it may deactivate the metathesis catalyst. More preferable temperature is 10 to 200° C., still more preferably 20 to 180° C., most preferably 60 to 180° C.

The metathesis polymerization process of the present invention is effected preferably in an inert gas atmosphere, but may be effected in air when the stable catalyst is used.

The polymer produced by the metathesis reaction, having a double bond, may be deteriorated by oxygen in air. The polymerization system may be incorporated with an anti-oxidant to prevent the deterioration.

The anti-oxidant useful for the present invention is not limited, so long as it is harmless to the metathesis polymerization reaction. The preferable ones include pentaerythritol-tetrakis [3-(3-di-t-butyl-4-hydroxyphenyl)propionate], 1,3,5-trimethyl-2,4,6-tris(3,5-t-butyl-4-hydroxybenzyl)benzene, 2,6-di-t-butyl-4-methyl phenol, tris-(3,5-di-t-butyl-4-hydroxybenzyl)isocyanurate and 1,3,5-tris(4-t-butyl-3-hydroxy-2,6-dimethylbenzyl)isocyanurate.

Content of the anti-oxidant is not limited. However, it is incorporated normally at 20 to 0.01% by weight of the whole composition in the polymerization system, preferably 5 to 0.1% by weight.

The organometallic compound catalyst of the present invention has another advantage, when used for polymerization of a monomer, e.g., DCPD, to produce a thermosetting resin which needs reaction molding, because it can give a curing speed more suitable for molding process than does the conventional ruthenium-based catalyst, with the result that addition of a third component, e.g., retardant, is not essential.

The polymer or its composition produced by polymerizing a metathesis-reactive monomer, e.g., norbornene, in the presence of the organometallic compound catalyst of the present invention is excellent in adhesion, resistance to heat, resistance to chemicals and so on, and can be used for various areas which need these characteristics, e.g., electrical/electronic parts, baths and combined purification tanks.

The metathesis-polymerized polymer or its composition produced in the presence of a reaction-controlling agent in addition to a metathesis-reactive monomer, e.g., norbornene, can be used for still wider areas which need these characteristics (adhesion, resistance to heat, resistance to chemicals and so on) than the one produced in the absence of such an agent, because its degree of polymerization can be freely controlled by adequately selecting type and content of the agent.

The metathesis-polymerized polymer or its composition produced in the presence of a reaction-controlling agent can be also used as function-donating agents, e.g., plasticizer and molding aid, because of its controlled molecular weight.

The metathesis-polymerized polymer produced in the presence of the organometallic compound of the present invention can be designed for various properties, e.g., melting and glass transition temperature, by copolymerizing two or more types of metathesis-reactive monomers, to still widen its applicable areas as function-donating agents.

EXAMPLES AND COMPARATIVE EXAMPLES

The present invention is described more specifically by EXAMPLES. However, it should be understood that the present invention is not limited to EXAMPLES.

Examples 1 to 15

In EXAMPLES 1 to 15, the organometallic compounds were synthesized by the reaction (ii) or (iii) to have the structure represented by one of the formulae (3) to (17). Table 1 summarizes the organometallic compound structures prepared in EXAMPLES, and metallic elements, ligands, substituents and the like in the general formula (2).

In EXAMPLE 1, the organometallic compounds represented by the formula (3) were synthesized by the reactions (ii) and (iii). These compounds were found to be identical to each other, as discussed later in Sections (A) and (B).

The objective organometallic compounds were prepared in EXAMPLES 2 to 13 and EXAMPLE 15 by the reaction (ii) or (iii) in the same manner as in EXAMPLE 1 except that the starting material was changed. The reaction (iii) involves a disadvantage in that a sterically bulky ligand, e.g., N,N'-dimethylimidazolium carbene, is difficult to introduce. By contrast, the reaction (ii) can easily introduce such a ligand. Accordingly, the organometallic compound was prepared by the reaction (ii) in EXAMPLE 14.

Each of these organometallic compounds was identified by, e.g., the elementary and NMR spectral analysis. The analysis results are described together after Table 1.

The NMR spectral analysis was conducted using a Varian Mercury 300 spectrometer under the conditions of chemical Shifts δ (ppm), 25° C., and standard of 1H-NMR: $SiMe_4$, 31P{1H} NMR: 85% $H_3PO_4$.

(A) Synthesis of the Organometallic Compound Represented by the Formula (3) (by the Reaction (ii))

(A-1) A mixture of 0.006 mols of Ru(p-cymene)$Cl_2$ to which 0.012 mols of tricyclohexylphosphine and 0.06 mols of acetonitrile were added was heated in the presence of 20 g of toluene in a 100 mL flask in a flow of nitrogen at 80° C. for 6 hours for the reactions. On completion of the reaction process, the produced precipitates were recovered and washed to isolate the complex (yield: 78%). The analysis indicated that it had a structure represented by the formula (a):

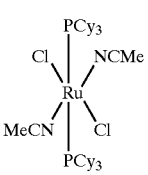

1H-NMR (CDCl$_3$) δ=1.25, 1.71 to 2.18, 2.54 (each m, 66H) 2.39 (s, 6H, $CH_3CN$): 31P {1H} NMR (CDCl$_3$) δ=11.28(s). Elementary analysis: C40H72Cl2N2P2Ru: Calculated composition C: 58.95%, H: 8.91% and N: 3.44%, Observed composition C: 59.11%, H: 9.03% and N: 3.33%

(A-2) A mixture of 0.006 mmols of the organometallic compound represented by the formula (a) to which 0.009 mols of 1-trimethylsilylhexyl was added was heated in the presence of dichloroethane as a solvent at 60° C. for 1 hour. The reaction effluent solution was treated to remove the solvent, and the resultant solids were recrystallized in a THF/ethanol system, to isolate the complex (yield: 78%). The analysis indicated that it had a structure represented by the formula (3), described later.

1H-NMR (CDCl$_3$) δ=0.10 (s, 9H, —SiMe$_3$), 0.85 (t, J=6.9 Hz, 3H, —C$_3$H$_6$—CH$_3$), 1.25, 1.56 to 1.79, 2.06 (each m, 60H, PCy$_3$, and 4H, —CH$_3$—C$_2$H$_4$—CH$_3$) 2.22 (bt, 2H, —CH$_2$—C$_3$H$_7$) 2.61 (bt, 6H, PCy$_3$): 31P {1H} NMR (CDCl$_3$) δ=19.90(s), Elementary analysis: C45H84Cl2P2SiRu: Calculated composition C: 60.92% and H: 9.54%, Observed composition C: 60.62% and H: 9.50%

(B) Synthesis of the Organometallic Compound Represented by the Formula (3) (by the Reaction (iii))

A mixture of 1.87 g (0.006 mols) of Ru(p-cymene)$Cl_2$ to which 3.42 g (0.012 mols) of tricyclohexylphosphine and 1.67 g (0.009 mols) of triisopropylsilylacetylene were added was heated in the presence of 20 g of toluene in a 100 mL flask in a flow of nitrogen at 80° C. for 24 hours for the reactions. On completion of the reaction process, toluene was distilled off under a vacuum, and the resultant solids were recrystallized in a THF/ethanol system, to synthesize 4.8 g of the organometallic compound (yield: 75%). The analysis indicated that it had a structure represented by the formula (3), described later. It had a composition of C: 62.01% and H: 9.59% (theoretical composition is C: 61.08% and H: 9.69%), as determined by the elementary analysis.

TABLE 1

| | M | $L_3$ | $L_4$ | $X_3$ | $X_4$ | $R_5$ | $R_6$ | $R_7$ | $R_8$ | formula |
|---|---|---|---|---|---|---|---|---|---|---|
| EXAMPLE 1 | Ru | $PCy_3$ | $PCy_3$ | Cl | Cl | nBu | Me | Me | Me | 3 |
| EXAMPLE 2 | Ru | $PCy_3$ | $PCy_3$ | Cl | Cl | Ph | Me | Me | Me | 4 |
| EXAMPLE 3 | Ru | $PCy_3$ | $PCy_3$ | Cl | Cl | nPr | Me | Me | Me | 5 |
| EXAMPLE 4 | Ru | $PCy_3$ | $PCy_3$ | Cl | Cl | Me | Me | Me | Me | 6 |
| EXAMPLE 5 | Ru | $PCy_3$ | $PCy_3$ | Cl | Cl | $SiMe_3$ | Me | Me | Me | 7 |
| EXAMPLE 6 | Ru | $PCy_3$ | $PCy_3$ | Cl | Cl | p-MeOPh | Me | Me | Me | 8 |
| EXAMPLE 7 | Ru | $PCy_3$ | $PCy_3$ | Cl | Cl | $CH_2OMe$ | Me | Me | Me | 9 |
| EXAMPLE 8 | Ru | $PCy_3$ | $PCy_3$ | Cl | Cl | SPh | Me | Me | Me | 10 |
| EXAMPLE 9 | Ru | $PCy_3$ | $PCy_3$ | Cl | Cl | 1-cyclohexenyl | Me | Me | Me | 11 |
| EXAMPLE 10 | Ru | $PCy_3$ | $PCy_3$ | Cl | Cl | COOH | Me | Me | Me | 12 |
| EXAMPLE 11 | Ru | $PCy_3$ | $PCy_3$ | Cl | Cl | H | iPr | iPr | iPr | 13 |
| EXAMPLE 12 | Ru | $PCy_3$ | $PCy_3$ | Cl | Cl | H | tBu | Me | Me | 14 |
| EXAMPLE 13 | Ru | $PCy_3$ | $PCy_3$ | Cl | Cl | H | Ph | Ph | Me | 15 |
| EXAMPLE 14 | Ru | Imes | $PCy_3$ | Cl | Cl | Ph | Me | Me | Me | 16 |
| EXAMPLE 15 | Os | $PCy_3$ | $PCy_3$ | Cl | Cl | Ph | Me | Me | Me | 17 |

In Table 1, IMes introduced as $L_3$ in EXAMPLE 14 is a ligand represented by the formula (18):

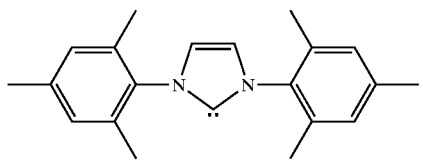
(18)

The organometallic compounds given in Table 1 have a structure represented by one of the formulae (3) to (17).

(3)

(4)

(5)

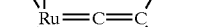
(6)

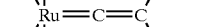
(7)

(8)

-continued (9)
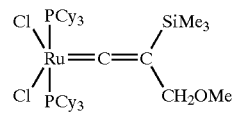

(10)
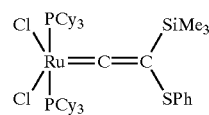

(11)

(12)

(13)

(14)
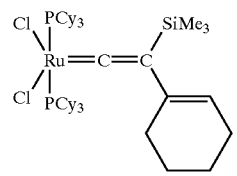

(15)
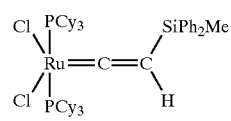

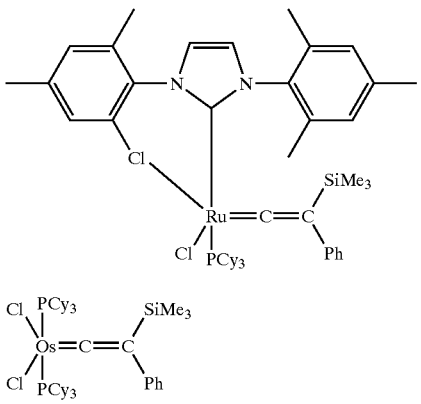

(16)

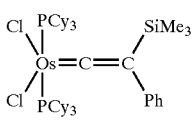

(17)

The organometallic compounds given in Table 1, represented by one of the formulae (3) to (17), had the following NMR spectral and elementary analysis results:

Organometallic Compound Represented by the Formula (4)

1H-NMR (CDCl$_3$) δ=0.29 (s, 9H, —SiMe$_3$), 1.20, 1.49 to 1.82, 2.09, 2.65 (each m, 66H, PCy$_3$), 7.09 to 7.28 (each m, 5H, Ph): 31P {1H} NMR (CDCl$_3$) δ=20.60(s). Elementary analysis: C47H80Cl2P2SiRu: Calculated composition C: 62.23% and H: 8.89%, Observed composition C: 61.97% and H: 8.78%

Organometallic Compound Represented by the Formula (5)

1H—NMR (CDCl$_3$) δ=0.10 (s, 9H, —SiMe$_3$), 0.84 (t, J=7.2 Hz, 3H, —C$_2$H$_4$—CH$_3$), 1.25, 1.56 to 1.79, 2.06 (each m, 60H, PCy$_3$, and 2H, —CH$_2$—CH$_2$—CH$_3$) 2.20(bt,2H, —CH$_2$—C$_2$H$_5$) 2.61 (bt, 6H, PCy$_3$): 31P {1H} NMR (CDCl$_3$) δ=19.84(s). Elementary analysis: C44H82Cl2P2SiRu: Calculated composition C: 60.52% and H: 9.47%, Observed composition C: 60.22% and H: 9.42%

Organometallic Compound Represented by the Formula (6)

1H-NMR (CDCl$_3$) δ=0.10 (s, 9H, —SiMe$_3$), 1.25, 1.56 to 1.79, 2.06 (each m, 60H) 2.20 (s, 3H, —CH$_3$) 2.61 (bt, 6H, PCy$_3$): 31P {1H} NMR (Toluene) δ=20.93(s). Elementary analysis: C42H78Cl2P2SiRu: Calculated composition C: 59.69% and H: 9.30%, Observed composition C: 59.39% and H: 9.26%

Organometallic Compound Represented by the Formula (7)

1H-NMR (CDCl$_3$) δ=0.17 (s, 18H, —SiMe$_3$), 1.25, 1.59 to 1.78, 2.09, 2.68 (each m, 66H, PCy$_3$): 31P {1H} NMR (CDCl$_3$) δ=20.97(s). Elementary analysis: C44H84Cl2P2Si2Ru: Calculated composition C: 58.51% and H: 9.37%, Observed composition C: 58.41% and H: 9.34%

Organometallic Compound Represented by the Formula (8)

1H-NMR (CDCl$_3$) δ=0.27 (s, 9H, —SiMe$_3$), 1.20, 1.60 to 1.68, 2.06, 2.65 (each m, 66H, PCy$_3$): 3.74 (s, 3H, —OMe$_3$), 6.71, 7.14 (each d, J=8.4 Hz, 2H, C$_6$H$_4$): 31P {1H} NMR (CDCl$_3$) δ=20.09(s). Elementary analysis: C48H82Cl2P2OSiRu: Calculated composition C: 61.51% and H: 8.82%, Observed composition C: 61.31% and H: 8.78%

Organometallic Compound Represented by the Formula (9)

1H-NMR (CDCl$_3$) δ=0.27 (s, 9H, —SiMe$_3$), 1.20, 1.60 to 1.68, 2.06, 2.65 (each m, 66H, PCy$_3$): 3.50 (s, 3H, —OMe), 4.01 (s, 2H, —CH$_2$—O): 31P {1H} NMR (CDCl$_3$) δ=20.89 (s). Elementary analysis: C41H74Cl2P2OSiRu: Calculated composition C: 58.27% and H: 8.83%, Observed composition C: 58.11% and H: 8.79%

Organometallic Compound Represented by the Formula (10)

1H-NMR (CDCl$_3$) δ=0.29 (s, 9H, —SiMe$_3$), 1.20, 1.49 to 1.82, 2.09, 2.65 (each m, 66H, PCy$_3$), 7.09 to 7.28 (each m, 5H, Ph): 31P {1H} NMR (CDCl$_3$) δ=20.60(s). Elementary analysis: C47H80Cl2P2SiRu: Calculated composition C: 62.23% and H: 8.89%, Observed composition C: 61.97% and H: 8.78%

Organometallic Compound Represented by the Formula (11)

1H-NMR (CDCl$_3$) δ=0.30 (s, 9H, —SiMe$_3$), 1.20, 1.49 to 1.82, 2.05 to 2.10, 2.65 (each m, 74H, PCy$_3$ and >C═CH—(CH$_2$)$_4$—), 6.21 (bt, 1H, >C═CH—): 31P {1H} NMR (CDCl$_3$) δ=19.10(s). Elementary analysis: C47H84Cl2P2SiRu: Calculated composition C: 61.95% and H: 9.29%, Observed composition C: 61.77% and H: 8.98%

Organometallic Compound Represented by the Formula (12)

1H-NMR (CDCl$_3$) δ=0.32 (s, 9H, —SiMe$_3$), 1.15, 1.52 to 1.79, 2.10, 2.68 (each m, 66H, PCy$_3$): 31P {1H} NMR (CDCl$_3$) δ=21.60(s). Elementary analysis: C42H76Cl2O2P2SiRu: Calculated composition C: 57.64% and H: 8.75%, Observed composition C: 57.27% and H: 8.88%

Organometallic Compound Represented by the Formula (13)

1H-NMR (CDCl$_3$) δ=1.02 (d, J=2.4 Hz, 18H, —CH(CH$_3$)$_2$), 1.23, 1.57 to 1.78, 2.08, 2.68 (each m, 66H, PCy$_3$, and 3H, —CH(CH$_3$)$_2$), 2.81 (t, $^4$J$_{PH}$=3 Hz, 1H, ═C═CH): 31P {1H} NMR (CDCl$_3$) δ=21.42(s). Elementary analysis: C47H88Cl2P2SiRu: Calculated composition C: 61.68% and H: 9.69%, Observed composition C: 61.56% and H: 9.64%

Organometallic Compound Represented by the Formula (14)

1H-NMR (CDCl$_3$) δ=0.09 (s, 6H, —SiMe$_2$), 0.81 (s, 9H, —SitBu), 1.25, 1.57 to 1.79, 2.09, 2.68 (each m, 66H, —PCy$_3$), 2.90 (t, $^4$J$_{PH}$=3 Hz, 1H, ═C═CH): 31P {1H} NMR (CDCl$_3$) δ=21.46(s). Elementary analysis: C44H82Cl2P2SiRu: Calculated composition C: 60.52% and H: 9.47%, Observed composition C: 60.75% and H: 9.55%

Organometallic Compound Represented by the Formula (15)

1H-NMR (CDCl$_3$) δ=0.68 (s, 3H, —SiMe), 1.92, 1.50 to 1.69, 2.08, 2.64 (each m, 66H, —PCy$_3$), 3.44 (t, $^4$J$_{PH}$=3 Hz, 1H, ═C═CH): 7.24 to 7.32, 7.48 to 7.51 (each m, 10H, —Ph): 31P {1H} NMR (CDCl$_3$) δ=22.07(s). Elementary analysis: C51H80Cl2P2SiRu: Calculated composition C: 64.13% and H: 8.44%, Observed composition C: 63.92% and H: 8.40%

Organometallic Compound Represented by the Formula (16)

1H-NMR (CDCl$_3$) δ=0.29 (s, 6H, —SiMe$_3$), 1.20, 1.49 to 1.83, 2.11, 2.64 (each m, 33H, PCy$_3$), 1.82 (s, 6H, p-Me-Mesythyl), 2.25 (s, 12H, o-Me-Mesythyl) 6.22 (s, 2H, ═CH—) 6.99 (s, 4H, m-H-Mesythyl) 7.11 to 7.38 (each m, 5H, Ph): 31P {1H} NMR (CDCl$_3$) δ=33.60(s). Elementary analysis: C50H71Cl2N2PSiRu: Calculated composition C: 64.49%, H: 7.68% and N: 3.01%, Observed composition C: 64.77%, H: 7.78% and N: 3.05%

Organometallic Compound Represented by the Formula (17)

1H-NMR (CDCl$_3$) δ=0.25 (s, 9H, —SiMe$_3$), 1.20, 1.49 to 1.90, 2.05, 2.70 (each m, 66H, PCy$_3$), 7.05 to 7.32 (each m, 5H, Ph): 31P {1H} NMR (CDCl$_3$) δ=22.60(s). Elementary analysis: C47H80Cl2P2SiOs: Calculated composition C: 56.66% and H: 8.09%, Observed composition C: 56.88% and H: 8.11%

Example 16

The organometallic compound having a structure represented by the formula (19) was synthesized in EXAMPLE 16 by the reaction (i).

0.006 mols of RuCl$_2$(PPh$_3$)$_3$ was reacted with 0.006 mols of trimethylsilyldiazomethane in 20 mL of methylene chloride at −78° C. for 5 minutes. Then, the reaction effluent solution was heated to room temperature, to which 0.0132 mols of tricyclohexylphosphine was added, and they were reacted with each other for 30 minutes. On completion of the reaction process, the effluent solution was treated to distill off the solvent under a vacuum, and the resultant solids were recrystallized in a methylene chloride/methanol system, to isolate the complex (yield: 75%). The analysis indicated that it had a structure represented by the formula (19).

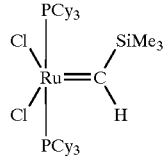
(19)

1H-NMR (CDCl$_3$) δ=0.20 (s, 9H, —SiMe$_3$), 1.18, 1.49 to 1.72, 2.64 (each m, 66H, PCy$_3$), 19.8 (s, Ru═CH, 1H, Ph): 31P {1H} NMR (CDCl$_3$) δ=19.60(s). Elementary analysis: C40H76Cl2P2SiRu: Calculated composition C: 58.65% and H: 9.35%, Observed composition C: 58.60% and H: 9.15%

Table 2 summarizes the organometallic compound structure prepared in EXAMPLE 16, and metallic element, ligands, substituents and the like in the general formula (1).

TABLE 2

| | M | L$_1$ | L$_2$ | X$_1$ | X$_2$ | R$_1$ | R$_2$ | R$_3$ | R$_4$ | formula |
|---|---|---|---|---|---|---|---|---|---|---|
| EXAMPLE 16 | Ru | PCy$_3$ | PCy$_3$ | Cl | Cl | nBu | Me | Me | Me | 19 |

Examples 17 to 19

The metathesis polymerization of DCPD was effected using the organometallic compound of the present invention in each of EXAMPLES 17 to 19, to evaluate the resultant polymer.

0.1 mmols (1/10,000 mols of DCPD) of the organometallic compound represented by the formulae (3), (4) or (13) was dissolved in 0.5 g of toluene, to which 132 g of DCPD was added. The mixture was then poured into a container via a 4 mm thick spacer, where it was kept at 80° C. for 1 hour, and then left at 120° C. for 1 hour, to prepare the polymer as the sample for property evaluation. It was measured by the dynamic viscoelasticity testing method (stretching method (n=1) using a viscoelasticity spectrometer in accordance with JIS K-7198), to determine temperature at which the tan δ value attained a maximum. The temperature level was used as glass transition temperature of the resin.

The sample (0.5 g) was taken from the polymer produced, and put in a 10 ml measuring flask, to which toluene was added to a given level. The mixture was left at room temperature for 20 hours, and the residual monomer was extracted and filtered by a 0.2 μm filter, to prepare the test piece. The residual monomer was measured by the following quantitative analysis.

[Quantitative Analysis]

The calibration solutions of 0.01, 0.1 and 0.5% (weight/volume %) of DCPD were prepared, and each was diluted with toluene and quantitatively analyzed by the absolute calibration line method (least square method). Each calibration solution was analyzed by gas chromatography under the following conditions. Residual monomer content was determined by the following formula:

Residual monomer content (% by weight)=(GC-detected quantity (weight/volume %)×10 mL)/sample weight (g)

Analyzer: Gas chromatograph (Shimadzu Corp.'s GC14A)
DCPD-analyzing column and temperature
Column: THERMON-3000, 5% SHINCARBON60/80 mesh, 2.1M,
I.D.: 3.2 mm
Temperature:
  Column: 100° C. (1 minute)~(10° C./minute)~150° C. (1 minute)
  Inlet port: 200° C.,
  Detector section: 200° C.
Carrier gas:
  He: 60 kPa, Combustion gases: Air 60 kPa, H$_2$ 60 kPa
  Carrier flow rate: He 55 cm$^3$/minute Table 3, described later, summarizes the tan δ peak temperature levels and residual monomer contents, determined by the above procedures.

Example 20

91 mg (1/10,000 mols of DCPD) of the ruthenium complex of the present invention, represented by the formula (4), was dissolved in 0.5 g of toluene, to which 132 g of DCPD and then 1 ml of 0.1N hydrochloric acid were added. The mixed solution was stirred at 40° C. for 5 minutes, and then poured into a container via a 4 mm thick spacer, where it was kept at 80° C. for 1 hour, and then left at 120° C. for 1 hour, to prepare the sample for property evaluation. It was measured in the same manner as in EXAMPLES 17 to 19. Table 3, described later, summarizes the measured tan δ peak temperature levels and residual monomer contents.

Comparative Example 1

An attempt was made to synthesize a polymer using the organometallic compound represented by the formula (20), described in Japanese Patent Laid-Open No.11-510807, in the same manner as in EXAMPLES 17 to 19, and to evaluate product properties. However, the polymerization reaction proceeded too fast to obtain the sample for tan δ peak evaluation. Only the residual monomer content is reported for this sample in Table 3, described later.

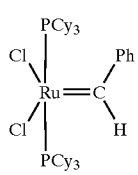
(20)

Comparative Examples 2 to 3

A polymer was synthesized and evaluated in each of COMPARATIVE EXAMPLES 2 to 3 using the organometallic compound, represented by the formula (21) or (22) and described in Japanese Patent Laid-Open No.11-510807, in the same manner as in EXAMPLES 17 to 19. Table 3, described later, summarizes the measured tan δ peak temperature levels and residual monomer contents.

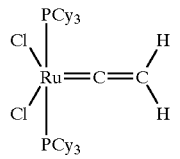
(21)

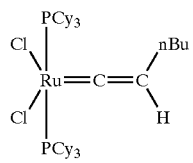
(22)

Comparative Example 4

A polymer was synthesized and evaluated in COMPARATIVE EXAMPLE 4 using the organometallic compound, represented by the formula (23) and described in Organometallics, 1998, 17, 5190, in the same manner as in EXAMPLES 17 to 19. Table 3, described later, summarizes the measured tan δ peak temperature level and residual monomer content.

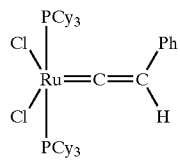
(23)

TABLE 3

|  | Complex | Tan δ | Residual monomer content |
|---|---|---|---|
| EXAMPLE 17 | 3 | 154° C. | 0.30% |
| EXAMPLE 18 | 4 | 156° C. | 0.30% |
| EXAMPLE 19 | 13 | 157° C. | 0.20% |
| EXAMPLE 20 | 4 | 158° C. | 0.10% |
| COMPARATIVE EXAMPLE 1 | 20 | — | 2.50% |
| COMPARATIVE EXAMPLE 2 | 21 | 139° C. | 1.50% |
| COMPARATIVE EXAMPLE 3 | 22 | 133° C. | 2.30% |
| COMPARATIVE EXAMPLE 4 | 23 | 141° C. | 1.80% |

It is confirmed, as shown in Table 3, that the metathesis reaction in the presence of the organometallic compound of the present invention gives a polymer of higher tan δ peak temperature than the one in the presence of the conventional metathesis catalyst. It is also confirmed that it leaves the residual monomer to a very low extent. These favorable results are attributable to the organometallic compound of the present invention, because it is highly resistant to heat and deactivated less in a DCPD polymerization process, which is known to be exothermic and operates at high temperature. Comparing the results of EXAMPLE 17 and 18 with those of respective COMPARATIVE EXAMPLES 3 and 4, it is demonstrated that the organometallic compound of the present invention is more reactive, when incorporated with silicon. Moreover, the effect of a reaction-adjusting agent is observed, when the results of EXAMPLE 18 are compared with those of EXAMPLE 20.

Examples 21 to 24

In each of EXAMPLES 21 to 24, DCPD was metathesis-polymerized in the presence of the organometallic compound of the present invention, as described below, to evaluate moldability of the polymer product.

0.1 mmols ($1/10,000$ mols of DCPD) of the organometallic compound of the present invention, represented by the formula (3), (5), (9) or (11), was dissolved in 0.5 g of toluene, and added to 132 g of DCPD contained in a 100 mL beaker, and the solution was heated at 60° C. The polymerization proceeded while it was stirred by stirrer chips for several minutes, and it started to form threads when the liquid surface was spooned up by a spatula. However, it no longer formed threads when its viscosity increased to a certain level; it repelled, like rubber, a spatula put in the solution to spoon up the surface. Gelation time is defined as a time span from start of the reaction to a point at which the solution no longer forms threads. It was used as a relative index which represented time span from start of the polymerization to a point at which the solution becomes moldable, to evaluate moldability of the polymer prepared in the presence of each catalyst. The results are given in Table 4, described later.

Comparative Examples 5 to 7

A polymer was synthesized in each of COMPARATIVE EXAMPLES 5 to 7 using the organometallic compound, represented by the formula (20), (21) or (22) and described in Japanese Patent Laid-Open No.11-510807, and its gelation time was measured in the same manner as in EXAMPLES 21 to 24, to evaluate moldability of the polymer prepared in the presence of each catalyst. The results are given in Table 4, described later.

TABLE 4

| Evaluation Item | EXAMPLE 21 | EXAMPLE 22 | EXAMPLE 23 | EXAMPLE 24 | COMPARATIVE EXAMPLE 5 | COMPARATIVE EXAMPLE 6 | COMPARATIVE EXAMPLE 7 |
|---|---|---|---|---|---|---|---|
| Complex | 3 | 5 | 9 | 11 | 20 | 21 | 22 |
| Gelation time | 6 minutes | 6 minutes | 5 minutes | 7 minutes | 10 seconds | 11 minutes | 12 minutes |

An ideal gelation time is around 5 minutes for producing various types of polymers, when they are to be molded into various shapes while DCPD is polymerized. When the reaction solution is gelled in a shorter time, it may be completely cured before it reaches every part in the mold, making it difficult to produce a desired molded article. When it is gelled in an excessively longer time, on the other hand, the process efficiency may be deteriorated.

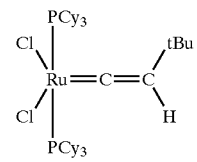

(24)

TABLE 5

| | Complex | Reaction-controlling agent content | Product yield | Number-average molecular weight (Mn) | Molecular weight distribution (PDI) |
|---|---|---|---|---|---|
| EXAMPLE 25-1 | 3 | 50 mmol | >99% | 7760 | 3.76 |
| EXAMPLE 25-2 | 3 | 100 mmol | >99% | 4828 | 3.04 |
| COMPARATIVE EXAMPLE 8-1 | 20 | 50 mmol | >99% | 69873 | 18.3 |
| COMPARATIVE EXAMPLE 8-2 | 20 | 100 mmol | >99% | 54839 | 15.4 |
| COMPARATIVE EXAMPLE 9-1 | 22 | 50 mmol | 60% | 8263 | 4.01 |
| COMPARATIVE EXAMPLE 9-2 | 22 | 100 mmol | 55% | 3987 | 3.56 |
| COMPARATIVE EXAMPLE 10-1 | 24 | 50 mmol | 73% | 25384 | 10.8 |
| COMPARATIVE EXAMPLE 10-2 | 24 | 100 mmol | 70% | 19987 | 9.81 |

As shown in Table 2, the polymer prepared in COMPARATIVE EXAMPLE 5 in the presence of the organometallic compound represented by the formula (20) is gelled too fast, suggesting that it will be difficult to mold the polymer into a desired shape. On the other hand, the one prepared in each of COMPARATIVE EXAMPLES 6 and 7 in the presence of the respective organometallic compound represented by the formula (21) or (22) needs an excessively long reaction time, suggesting that it may cause significant process problems. By contrast, it is demonstrated that the metathesis polymerization reaction in each of EXAMPLES 21 to 24, which proceeds in the presence of the organometallic compound represented by the formula (3), (5), (9) or (11), is useful for producing desired molded shape for adequate gelation time of the polymer it gives.

Example 25

0.5 mmols of the organometallic compound of the present invention, represented by the formula (3), was put in a 500 mL egg-plant type flask, to which 1.0 mol of norbornene, 100 mL of toluene and 50 or 100 mmols of allyl acetate as a reaction-controlling agent were added, and the mixture was kept at 40° C. for the ring-opening metathesis polymerization. The product polymer was analyzed for the product yield, number-average molecular weight (Mn) and molecular weight distribution (PDI) to evaluate the effect of the reaction-controlling agent. The results are given in Table 5, described later, where these polymer products are designated as those prepared in EXAMPLES 25-1 or 25-2.

Comparative Examples 8 to 10

The polymers synthesized in the presence of the organometallic compound represented by the formula (20) or (21) described in Japanese Patent Laid-Open No.11-510807, or of the one represented by the formula (24) described in Chem. Lett., 1999, 369 were evaluated in the same manner as in EXAMPLE 25. The results are given in Table 5, described later, where these polymer products are designated as those prepared in COMPARATIVE EXAMPLES 8 to 10-1 or 8 to 10-2.

As shown in Table 5, the polymerization process of the present invention can give a polymer of controlled molecular weight, because it proceeds at an adequate rate in the presence of the organometallic compound of the present invention coupled with a reaction-controlling agent. In the similar process which uses the organometallic compound in COMPARATIVE EXAMPLE 8, on the other hand, a high-molecular-weight polymer is produced, because the complex is too active to control the reaction. Moreover, in the similar process which uses the organometallic compound in COMPARATIVE EXAMPLE 9, the complex is less active than the organometallic compound represented by the formula (3) of the similar structure except that it contains silicon, causing reduced product yield and slightly deteriorated controllability.

It may be difficult for the organometallic compound represented by the formula (24) as a catalyst to control the reaction at a very low content, e.g., 1/2000 mols per mol of the monomer as used in COMPARATIVE EXAMPLE 10, although exhibiting controllability at a very high content, e.g., 1/20 mols per mol of the monomer, as described in Chem. Lett., 1999, 369. On the other hand, the polymerization reaction controlled by the organometallic compound of the present invention as a catalyst, which contains silicon, can give a well-controlled polymer in a high yield even at a very low content of 1/2000 mols, and hence is advantageous industrially.

Examples 26 to 31

The NMR spectral analysis was conducted in each of EXAMPLES 26 to 31 to measure thermal stability of the organometallic compound of the present invention in a solution using a Varian Mercury 300 spectrometer under the conditions of chemical Shifts δ (ppm), 25° C., and standard of 1H-NMR: SiMe$_4$, 31P{1H} NMR: 85% H$_3$PO$_4$.

0.025 mmols of the organometallic compound represented by the formula (3), (7), (8), (10), (12) or (13) was put in a nitrogen-purged NMR tube, to which 0.6 mL of distilled toluene was added to dissolve the compound therein, and the solution was heated at 80° C. in a nitrogen atmosphere. The 31P{1H} NMR was measured immediately after it reached 80° C. and 6, 12 and 24 hours thereafter, to observe its temporal changes, and evaluate stability of each organometallic compound from the spectral intensity. The results are given in Table 6, described later.

Comparative Example 11

The organometallic compound represented by the formula (20) was evaluated in the same manner as in EXAMPLES 26 to 31. The results are given in Table 6, described later.

TABLE 6

| | Complex | Immediately after | 6 hours after | 12 hours after | 24 hours after |
|---|---|---|---|---|---|
| EXAMPLE 26 | 3 | 100% | 99% | 98% | 96% |
| EXAMPLE 27 | 7 | 100% | 98% | 95% | 90% |
| EXAMPLE 28 | 8 | 100% | 98% | 95% | 93% |
| EXAMPLE 29 | 10 | 100% | 95% | 90% | 85% |
| EXAMPLE 30 | 12 | 100% | 95% | 89% | 84% |
| EXAMPLE 31 | 13 | 100% | 99% | 97% | 95% |
| COMPARATIVE EXAMPLE 11 | 20 | 100% | 28% | 5% | — |

As shown in Table 6, the organometallic compound prepared in each of EXAMPLES 26 to 31 almost fully remained undecomposed for 24 hours, suggesting its excellent thermal stability. By contrast, the one prepared in COMPARATIVE EXAMPLE 11 was almost decomposed in 6 hours, and completely in 24 hours. These results indicate that the organometallic compound of the present invention is excellent in thermal stability.

POSSIBILITY OF INDUSTRIAL UTILIZATION

As described above, the organometallic compound of the present invention is excellent in resistance to heat and oxygen and also in reaction controllability, and high in metathesis activity. As such, the resin produced in the presence of the organometallic compound as a metathesis reaction catalyst has various advantages over that produced in the presence of the conventional metathesis reaction catalyst, e.g., higher glass transition temperature and lower residual monomer content to reduce its odor, and can be used for various areas which need characteristics of high adhesion, resistance to heat and chemicals, and so on, e.g., electrical/electronic parts, baths and combined purification tanks.

The present invention can control molecular weight of the polymer, a characteristic which the conventional metathesis reaction process is weak in, by the aid of a reaction-controlling agent. Such a polymer is applicable to adhesive agents and molding aids. Copolymerization of two or more types of metathesis-reactive monomers can greatly expand the process applicable range.

The organometallic compound catalyst of the present invention has another advantage, when used for polymerization of a monomer, e.g., DCPD, to produce a thermosetting resin which needs reaction molding, because it can give a curing speed more suitable for molding process than does the conventional ruthenium-based catalyst, with the result that addition of a third component, e.g., retardant, is not essential.

What is claimed is:
1. An organometallic compound containing ruthenium or osmium and silicon, represented by the general formula (1):

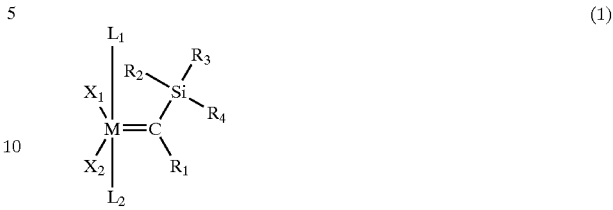

wherein, M is ruthenium or osmium; $R_1$ is hydrogen atom, an alkenyl group of 2 to 20 carbon atoms, alkyl group of 1 to 20 carbon atoms, aryl group of 6 to 20 carbon atoms, carboxyl group of 2 to 20 carbon atoms, alkoxy group of 2 to 20 carbon atoms, alkenyloxy group of 2 to 20 carbon atoms, aryloxy group of 6 to 20 carbon atoms, alkoxycarbonyl group of 2 to 20 carbon atoms, alkylthio group of 2 to 20 carbon atoms, alkylsilyl group of 2 to 20 carbon atoms, arylsilyl group of 2 to 20 carbon atoms or ferrocene derivative, as required, with a phenyl group substituted with an alkyl group of 1 to 5 carbon atoms, halogen atom or alkoxy group of 1 to 5 carbon atoms; $R_2$ to $R_4$ are each hydrogen atom, an alkenyl group of 2 to 20 carbon atoms, alkyl group of 1 to 20 carbon atoms, aryl group of 6 to 20 carbon atoms, carboxyl group of 2 to 20 carbon atoms, alkoxy group of 2 to 20 carbon atoms, alkenyloxy group of 2 to 20 carbon atoms, aryloxy group of 6 to 20 carbon atoms, alkoxycarbonyl group of 2 to 20 carbon atoms, alkylthio group of 2 to 20 carbon atoms, alkylsilyl group of 2 to 20 carbon atoms, arylsilyl group of 2 to 20 carbon atoms or ferrocene derivative, which may be the same or different and substituted, as required, with a phenyl group substituted with an alkyl group of 1 to 5 carbon atoms, halogen atom or alkoxy group of 1 to 5 carbon atoms; when $R_1$ is hydrogen atom, at least one of $R_2$ to $R_4$ is phenyl, isopropyl or t-butyl group; $X_1$ and $X_2$ are each an anionic ligand, which may be the same or different; and $L_1$ and $L_2$ are each a neutral electron donor, which may be the same or different and at least one of $L_1$ and $L_2$ is a phosphorus-based ligand; where 2 or 3 of $X_3$, $X_2$, $L_1$ and $L_2$ may together form a multidentate, chelated ligand.

2. The organometallic compound according to claim 1, wherein $R_1$ in the general formula (1) is a substituent selected from the group consisting of phenyl, anisyl, t-butyl, n-butyl, n-propyl, isopropyl, ethyl, methyl, methoxymethyl, ferrocenyl and trimethylsilyl group.

3. The organometallic compound according to claim 1, wherein each of $R_2$ to $R_4$ in the general formula (1) is a substituent selected from the group consisting of methyl, ethyl, isopropyl, t-butyl, cyclohexyl and phenyl group.

4. The organometallic compound according to claim 1, wherein each of $L_1$ and $L_2$ in the general formula (1) is a phosphorus-based ligand.

5. An organometallic compound containing ruthenium or osmium and silicon, represented by the general formula (2):

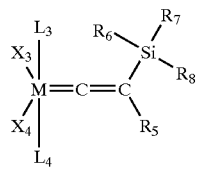

(2)

wherein, M is ruthenium or osmium; $R_5$ is hydrogen atom, an alkenyl group of 2 to 20 carbon atoms, alkyl group of 1 to 20 carbon atoms, substituted phenyl group of 7 to 20 carbon atoms, carboxyl group of 2 to 20 carbon atoms, alkoxy group of 2 to 20 carbon atoms, alkenyloxy group of 2 to 20 carbon atoms, aryloxy group of 6 to 20 carbon atoms, alkoxycarbonyl group of 2 to 20 carbon atoms, alkylthio group of 2 to 20 carbon atoms, alkylsilyl group of 2 to 20 carbon atoms or arylsilyl group of 2 to 20 carbon atoms; $R_6$ to $R_8$ are each hydrogen atom, an alkenyl group of 2 to 20 carbon atoms, alkyl group of 1 to 20 carbon atoms, aryl group of 6 to 20 carbon atoms, carboxyl group of 2 to 20 carbon atoms, alkoxy group of 2 to 20 carbon atoms, alkenyloxy group of 2 to 20 carbon atoms, aryloxy group of 6 to 20 carbon atoms, alkoxycarbonyl group of 2 to 20 carbon atoms, alkylthio group of 2 to 20 carbon atoms, alkylsilyl group of 2 to 20 carbon atoms, arylsilyl group of 2 to 20 carbon atoms or ferrocene derivative, which may be the same or different and substituted, as required, with a phenyl group substituted with an alkyl group of 1 to 5 carbon atoms, halogen atom or alkoxy group of 1 to 5 carbon atoms; when $R_5$ is hydrogen atom, at least one of $R_6$ to $R_8$ is phenyl, isopropyl or t-butyl group; $X_3$ and $X_4$ are each a halogen atom, which may be the same or different; and $L_3$ and $L_4$ are each a neutral electron donor, which may be the same or different; where 2 or 3 of $X_3$, $X_4$, $L_3$ and $L_4$ may together form a multidentate, chelated ligand.

6. The organometallic compound according to claim 5, wherein $R_5$ in the general formula (2) is a substituent selected from the group consisting of tolyl, anisyl, t-butyl, n-butyl, n-propyl, isopropyl, ethyl, methyl, methoxymethyl and trimethylsilyl group.

7. The organometallic compound according to claim 5, wherein each of $R_6$ to $R_8$ in the general formula (2) is a substituent selected from the group consisting of methyl, ethyl, isopropyl, t-butyl, cyclohexyl and phenyl group.

8. The organometallic compound according to claim 5, wherein each of $L_3$ and $L_4$ in the general formula (2) is a phosphorus-based ligand.

9. A process for producing the organometallic compound according to claim 1, wherein a precursor for a ruthenium or osmium complex and neutral electron-donating ligand compound are mixed with each other for the ligand-exchanging reaction.

10. A metathesis reaction catalyst containing the organometallic compound according to claim 1.

11. A metathesis polymerization process for producing a metathesis-reactive monomer in the presence of the metathesis reaction catalyst according to claim 10.

12. The metathesis polymerization process according to claim 11, wherein said metathesis-reactive monomer is a norbornene-based monomer of bicyclic or higher structure.

13. The metathesis polymerization process according to claim 11, wherein said norbornene-based monomer is a compound selected from the group consisting of norbornene, substituted norbornene, dicyclopentadiene and tricyclopentadiene.

14. The metathesis polymerization process according to one of claims 11 to 13, wherein 2 or more metathesis-reactive monomers are copolymerized.

15. The metathesis polymerization process according to one of claims 11 to 13, wherein a reaction-adjusting agent is further incorporated.

16. The metathesis polymerization process according to claim 15, wherein said reaction-adjusting agent is an acidic component.

17. The metathesis polymerization process according to claim 16, wherein said acidic component is a Bronsted acid (protonic acid).

18. The metathesis polymerization process according to one of claims 11 to 13, wherein a reaction-controlling agent is further incorporated.

19. The metathesis polymerization process according to claim 18, wherein said reaction-controlling agent is a compound having a metathesis-reactive unsaturated bond.

20. The metathesis polymerization process according to claim 19, wherein said compound having a metathesis-reactive unsaturated bond is selected from the group consisting of a vinyl ester, vinyl sulfide, vinyl ether, vinyl pyrrolidone, allyl ester and allyl sulfide.

* * * * *